United States Patent [19]

Farkas et al.

[11] 4,241,998
[45] Dec. 30, 1980

[54] SPECTROPHOTOMETER

[75] Inventors: Rudolf Farkas, Geneva; Michel Moulin, Lausanne; Georges Revillet, Onex, all of Switzerland

[73] Assignee: Hoffmann-La Roche Inc., Nutley, N.J.

[21] Appl. No.: 4,427

[22] Filed: Jan. 18, 1979

[30] Foreign Application Priority Data

Jan. 20, 1978 [CH] Switzerland .............................. 621/78
Nov. 16, 1978 [CH] Switzerland ........................ 11782/78

[51] Int. Cl.³ ............................................... G01J 3/42
[52] U.S. Cl. .................................................... 356/319
[58] Field of Search ................................ 356/319–326, 356/328, 330, 332, 334

[56] References Cited

U.S. PATENT DOCUMENTS

| | | | |
|---|---|---|---|
| 2,849,912 | 9/1958 | Plesse et al. ............................ | 356/408 |
| 2,981,826 | 4/1961 | Mattern ........................ | 350/96.15 X |
| 3,009,388 | 11/1961 | Polanyi ................................ | 356/245 |
| 3,599,002 | 8/1971 | Beutelspacher et al. ........... | 356/36 X |
| 3,637,310 | 1/1972 | Naono .................................... | 356/319 |
| 3,810,696 | 5/1974 | Hutchins, Jr. ......................... | 356/325 |
| 3,917,406 | 11/1975 | Siegler, Jr. ............................ | 356/319 |
| 4,022,534 | 5/1977 | Kishner ................................. | 356/446 |
| 4,068,954 | 1/1978 | Da Silva ............................... | 356/334 |
| 4,076,421 | 2/1978 | Kishner ................................. | 356/320 |

FOREIGN PATENT DOCUMENTS

| | | | |
|---|---|---|---|
| 2297431 | 8/1976 | France . | |
| 1078976 | 8/1967 | United Kingdom ..................... | 356/434 |
| 1111632 | 5/1968 | United Kingdom . | |
| 1126841 | 8/1968 | United Kingdom . | |
| 1181163 | 2/1970 | United Kingdom . | |

OTHER PUBLICATIONS

Wales et al., *Journal of Research of the National Bureau of Standards*, vol. 15, No. 2, Feb. 5, 1953, Research paper 2390, pp. 69–70.
De Sa et al., *The Review of Scientific Instruments*, vol. 37, No. 7, Jul. 1966, pp. 900–906.
Luthjens, *The Review of Scientific Instruments*, vol. 44, No. 11, Nov. 1973, pp. 1661–1665.

*Primary Examiner*—F. L. Evans
*Attorney, Agent, or Firm*—Jon S. Saxe; Bernard S. Leon; Mark L. Hopkins

[57] ABSTRACT

Spectrophotometer intended in particular for the optical analysis of samples in a rotatory analyser. In order to attain the characteristics required of a modern spectrophotometer for clinical chemistry and to attain in particular a high reproducibility of the measurements, the spectrophotometer comprises a flash tube, an stabilizing optical device for device for deriving a light beam having a constant spatial distribution from each flash from the flash tube, a grating monochromator for dispersing the light delivered by the stabilizing device and for delivering a beam of filtered light, an optical element for dividing the filtered beam to produce two beams, the first of which travels through a sample for analysis and the second of which reaches a detector which delivers a reference signal corresponding to the intensity of the second beam, and a second detector placed to receive the beam emerging from the sample.

9 Claims, 14 Drawing Figures

SPECTROPHOTOMETER

BACKGROUND OF THE INVENTION

The invention relates to a spectrophotometer.

More particularly, it relates to a spectrophotometer used for optical analysis of samples in a rotary analyzer.

In some double-beam spectrophotometers, the double beam is obtained by physical separation of a beam supplied by a monochromator (H. Moenke and L. Moenke—Blankenburg, "Optische Bestimmungsverfahren und Gerte,uml/a/te für Mineralogen und Chemiker", Akademische Verlagsgesellschaft Geest & Portig K.G., Leipzig 1965, pages 185-307). Separation into two beams is for the purpose of compensating variations in the intensity of the spectrophotometer light source. One beam is used as the reference intensity and the other travels through the sample to be measured.

There are various possibilities for the choice of the main components of spectrophotometers. The light source comprises one or two continuous-emission lamps, i.e. halogen, deuterium, mercury arc and/or xenon. Prism or grating dispersion devices are used for the monochromator. The detectors are generally photomultipliers or phototubes, or silicon photodiodes in certain more recent developments. The numerous kinds of available components and the various possible structures can be combined in numerous ways to construct a spectrophotometer.

The disadvantages of known spectrophotometers are mainly due to the light source and the monochromator used.

The tungsten-halogen lamp is undoubtedly the most frequently-used source for applications in the visible spectrum. However, it has the following well-known disadvantages:

Very weak emission in the ultraviolet light;

Very great variation of light intensity in the useful spectrum; the intensity of light at 290 nm is about 900 times less than at 700 nm;

The proportion of interfering light is considerable, which means that expensive blocking filters need to be used;

The system for compensating variations in light intensity with wavelength must have a wide dynamic range;

The service life is relatively short;

The light output is low: 8 lm/W;

The dissipated power is considerable, and

The electric supply means for the lamp is relatively heavy and bulky.

In order to obviate the difficulties encountered in the ultraviolet with the aforementioned kind of lamp, certain spectrophotometers use a second source of light, generally a deuterium lamp. This method, however, has the added disadvantages of high cost and considerable bulk.

Light is also obtained from lamps giving different kinds of electric discharges, e.g. xenon, mercury or argon lamps. Xenon lamps have the most uniform spectrum in the range required by the application, and their light efficiency is much greater than that of tungsten, e.g. 21 lm/W with a 150 W lamp. The lamps are usually supplied for higher power than 100 W, and are very difficult to cool. The lamp supply and mounting means are very voluminous and expensive.

The grating monochromator is the preferred method of continuously varying the wavelength. However, the proportion of interfering light resulting from the associated lamp and monochromator must be very low, less than $1.10^{-4}$ in practice, if it is desired to make measurements having a linearity error lower than 1.5% up to an attenuation of 1000 times (corresponding to an absorbance of 3). To obtain a performance of this kind, double-grating monochromators are used, since single-grating monochromators have too high a proportion of interfering light. However, double-grating monochromators are expensive, bulky and take a relatively long time to align.

The U.S. Pat. No. 3,810,696 discloses a spectrophotometer comprising a flash tube and an interference filter or a monochromator to produce two light beams, the first of which travels through a sample for analysis and the second of which reaches a detector which delivers a reference signal corresponding to the intensity of the second beam. The U.S. Pat. No. 3,810,696 contains no disclosure relative to neither difficulties or disadvantages which are caused by fluctuations of the position of the arc (in the flash tube) from one flash to the next one or to means placed between the flash tube and the monochromator to overcome such difficulties.

SUMMARY OF THE INVENTION

An object of the invention is to devise a spectrophotometer for a clinical chemical analyzer comprising a rotor rotating at approx. 1000 rpm and bearing small-volume samples. The spectrophotometer must have the following features, which are not satisfactorily obtained with any existing spectrophotometer:

(1) Measuring the absorbance of liquid samples deposited in cells rotating at approx. 1000 rpm;

(2) Brief duration of measurement of 30 samples on the rotor, i.e. in less than 350 milliseconds;

(3) Time available per measurement is less than 50 microseconds;

(4) Small volume of liquid sample: 200 microliters;

(5) Continuous selection of wavelengths between 290 and 700 nm;

(6) Bandwidth: 8 nm;

(7) Wide range of measurable absorbance, from 0.0 to 3.0.

These features are particularly important in automatic instruments in order to make up the considerable differences in absorbance between normal cases and pathological cases of biological material under examination—e.g. between a lypaemic serum and a normal serum.

(8) Reproducibility of measurements compatible with the requirements for enzyme reactions (standard deviation $\sigma < 5.10^{-4}$ absorbance unit). This refers to the reproducibility of measurements of absorbance on a single sample. This point is particularly important in the case of kinetic methods. In these methods the variation in absorbance is slow, i.e. the measurements can be speeded up if reproducibility is good. In these methods also, the absorbance level is sometimes quite high (1.7–2.2). Thus, reproducibility must be excellent over a wide range of absorbance.

(9) Excellent linearity between absorbance and concentration over a wide range of absorbance. This linearity simplifies the use of the instrument, in that a calibration curve is not needed. Linearity is difficult to obtain at high absorbance, specially in the ultraviolet. It depends on the purity of the monochromatic light, i.e. on the proportion of interfering light, which is defined by the ratio of (a) the intensity of residual light emitted outside the selected spectral band to (b) the intensity of light inside the selected spectral band.

(10) Small bulk. This is a desirable quality in the case of an instrument which is normally used in small, cluttered laboratories.

(11) Reduced maintenance, and

(12) Low cost.

In order to reduce the bulk and cost of the spectrophotometer, it is also desirable for the detectors to be silicone photodiodes associated with low-noise amplifiers.

The aforementioned photometric performance, if it has to be obtained during a relatively short measuring time, creates special technical difficulties relating to the required signal/noise ratio and to obtaining a light beam having the required spectral purity. In addition, owing to the shape of the sample-containing cells, it is necessary to use a light beam having a small cross-section over a relatively great length, thus limiting the numerical aperture of the optical system and consequently limiting the solid angle for collecting light from the source.

Since it is desired to make reproducible measurements with a maximum signal attenuation of 1000 times through the sample, it is necessary for the signal/noise ratio to be at least $2.10^{-5}$ at zero absorbance. Since the measurement is very short (less than 50 microseconds) an amplifier having a wide pass band is needed, which makes it difficult to obtain the desired signal/noise ratio since, as is known, the noise increases with the width of the amplifier pass-band. The effect of this noise is considerable compared with the effect of noise in conventional spectrophotometers, in which the influence of noise on the measured results can be reduced by integrating the measured signal over one or more seconds. The problem of obtaining an adequate signal/noise ratio is made even more difficult because it is desired to use silicone photodiodes, since the association of a photodiode with an amplifier is noisier than a photomultiplier operating at a weak signal level. This applies more particularly to wavelengths below 400 mm for measurements of high absorbance values (A=3), since silicone photodiodes have a lower sensitivity than photomultipliers in this part of the spectrum.

In order to obtain the photometric characteristics described hereinbefore, the light beam supplied by the monochromator must have very high spectral purity, in order to avoid the well-known problems of non-linearity due to interfering light and bandwidth effects. There are certain difficulties in obtaining a light beam having the spectral purity required for photometric purposes, if the cost and bulk of the spectrophotometer have to be simultaneously reduced. For these purposes it is desired to reduce the proportion of interfering light to a value of approx. $1.10^{-4}$ at a wavelength of 290 nm, using a grid monochromator having a short focal length (approx. 100 mm) with a spectral emission range limited by a filter between 270 and 380 nm.

The spectrophotometer according to the invention is characterised in that it comprises:

(a) a flash tube, (b) an stabilizing optical device for deriving a light beam having a constant spatial distribution from each flash from the flash tube, (c) a grating monochromator for dispersing the light delivered by the stabilizing device and for delivering a beam of filtered light, (d) an optical element for dividing the filtered beam to produce two beams, the first of which travels through a sample for analysis and the second of which reaches a detector which delivers a reference signal corresponding to the intensity of the second beam, and (e) a second detector placed to receive the beam emerging from the sample.

The spectrophotometer according to the invention can be used to obtain the aforementioned desired performance and has the following additional advantages:

(1) Very low power consumption and dissipation, thus reducing the cost and volume of the supply means, and the lamp can be incorporated in a very compact optical unit (see FIG. 6) owing to the absence of thermal constraints;

(2) Long service life of source (more than $20.10^6$ flashes) and of detectors, resulting in high reliability and low maintenance, and (3) No time required for stabilizing the emission of the lamp used as light source.

BRIEF DESCRIPTION OF THE DRAWINGS

Other features, advantages and possible applications of the invention will become apparent from the following description of embodiments, taken with reference to the accompanying drawings, in which.

DESCRIPTION OF THE PREFERRED EMBODIMENTS

Figure 1:
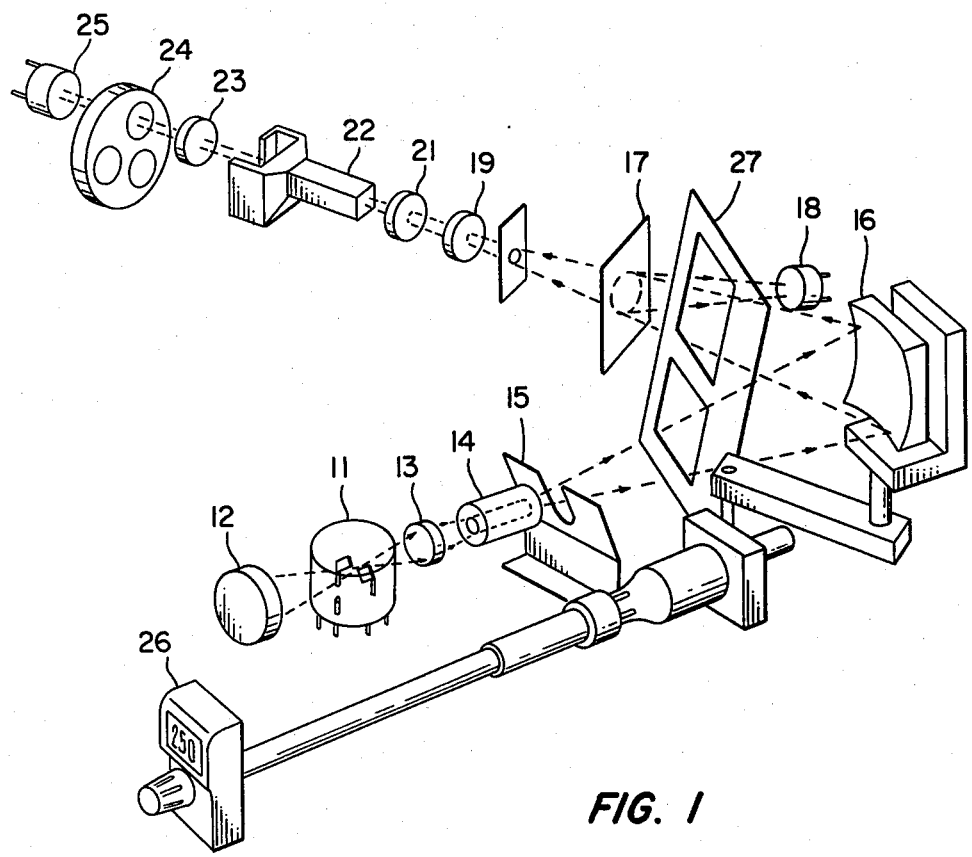
FIG. 1 is a perspective diagram of the optical system of a spectrophotometer according to the invention.

FIG. 1 is a diagrammatic perspective view of the optical system of a spectrophotometer according to the invention, comprising: a flash tube 11; an optical device comprising a spherical mirror 12; a lens 13 (focal length 8 mm, diameter 12.5 mm) and a tube 14, which optical device 15 is called the "stabilizing device" in this specification and is used for obtaining a constant spatial and angular distribution of the light supplied by the flash tube to a grating monochromator 16; a separating plate 17 which reflects part of the beam of light supplied by the monochromator to a silicon photodiode 18 to generate a reference signal, and transmits the remainder of the monochromator beam through lenses 19, 21 (each having a focal distance of 13 mm and a diameter of 8 mm); a cell 22 containing a sample; a lens 23 and one of the order filters 24 in front of a silicon photodiode 25 which supplies an electric signal corresponding to the intensity of the beam transmitted through the sample.

The optical system in FIG. 1 also comprises a zero-order diffracted light deflector 15, a mask 27 reducing interfering light and a device 26 for selecting and displaying the wave-length chosen for measurements.

Flash tube 11 is a xenon lamp for producing light pulses lasting approx. 2.3, $\mu$sec, which is considerably less than the time (>150, $\mu$sec) spent by a sample in the axis of the light beam in the case of a rapid rotary analyzer e.g. with a rotor holding 30 samples and rotating at 1000 rpm.

Flash tube 11 is of the bulb type and has a power of about 7 W. If the energy released per flash is 0.3 joules for 2.3 microseconds, the mean power emitted during these 2.3 microseconds is equivalent to that from a 130 kW continuous xenon lamp. Clearly, there is a gain in light level and consequently in the signal/noise ratio by using a pulsed lamp like flash tube 11. The advantages of using flash tube 11 may be summarised as follows:

A single light source for the entire spectrum;
Very low dissipated power;
Compact lamp and supply assembly;
Relatively uniform spectrum;
Long service life; and
Very high level of monochromatic light.

However, there are difficulties in using a source of pulsed light such as a flash tube, owing to the fact that the path of the arc between the electrodes of the tube varies at random from one flash to another, resulting in a variation in the emitted light energy and its spatial distribution. These variations must be reduced or compensated to obtain reproducible measurements in the case of a spectrophotometer.

Variations in light intensity are compensated by using a double beam, i.e. a beam travelling through the sample, and a reference beam, so that the variations do not substantially affect the results.

Figure 2:
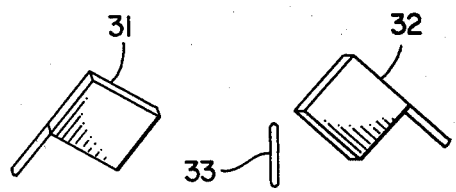
FIG. 2 shows a preferred arrangement of the electrodes of the flash tube 11 in FIG. 1.

In order to ensure that the arc between the electrodes of the flash tube has a spatial position, which is as stable as possible, it is advantageous to use a bulb-type flash tube where the distance between anode 31 and cathode 32 is of the order of 1.5 mm and/or a starting electrode 33 is disposed very near the cathode (see FIG. 2) e.g. 0.2 to 0.5 mm therefrom.

It is particularly advantageous to use a flash tube with an anode and a cathode having each the shape of a pastille, said pastilles being placed in the same plane and placed in such a way with respect to each other that the arc corresponding to each flash is formed between corners of said pastilles. A flash tube carrying the designation FX-233 U, manufactured by EG & G, Inc., Salem, Massachusetts, USA is used in the preferred embodiment of the invention described herein. alternatively, a flash tube carrying the designation XFX-119 U, of the same manufacturer, can also be used.

Figure 9:
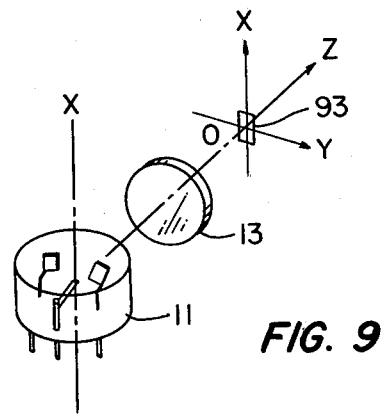
FIG. 9 shows a schematic representation of the optical arrangement from the flash tube to the input-slot of the monochromator, but without tube 14 shown in FIG. 1, and FIGS. 10a, 10b, 11a, 11b show typical variations of the spatial distribution of light intensity at the input-slot of the monochromator from one flash to the other, when the arrangement of FIG. 9 is used.

In order to reduce fluctuations in the spatial distribution of the flash intensity, it is also advantageous to dispose flash tube 11 so that the arcs produced between the electrodes thereof extend parallel to the width of the inlet slot 93 of the monochromator (see FIG. 9).

These two last features help to reduce variations in the wavelength of the beam delivered by the monochromator due to fluctuations in the position of the arc from one flash to another.

Figure 3:
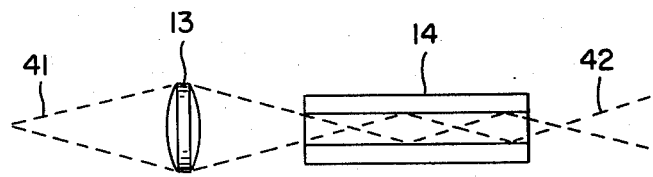
FIG. 3 is a diagrammatic view in section of part of the device for stabilizing the beam in the optical system in FIG. 1.

As previously mentioned, the device for stabilizing the beam in the optical system in FIG. 1 comprises a lens 13 (or condenser) which forms an image of the flash produced by flash tube 11 at the inlet of tube 14. As shown in FIG. 3, the light rays 41 are reflected by the inner walls of tube 14, giving practically a constant spatial distribution of light intensity of beam 42 at the outlet of tube 14. Preferably the stabilizing device is disposed to prevent light rays from the parts near the cathode and anode from entering tube 14, since the spatial position of light rays from the aforementioned parts is particularly unstable, i.e. varies appreciably from one flash to the next.

Tube 14 has light-reflecting internal walls. The image of the arc in the flash tube 11 is formed at the optical inlet of tube 14. The optical outlet of this tube coincides with the inlet slot of the monochromator. The inner dimensions of tube 14 correspond to those of the latter slot. The cross-section of tube 14 can be circular, square or rectangular. The successive reflexions of the light beam on the internal walls of tube 14 make it possible to provide at the optical outlet thereof a light beam 42 the intensity of which has a constant spatial distribution independently from fluctuations of the spatial distribution of light intensity at the optical inlet of tube 14 from one flash to the next.

This independance becomes greater when the chosen length of tube 14 is increased, but with a corresponding increase in the loss of light energy since the number of reflections also depends from the length of the tube. With a tube 14 having a length of 11 or 22 mm, a certain influence of fluctuations of the position of the arc in the flash tube on the reproducibility of the measurements is still observed, but a considerable improvement of the reproducibility is attained already with a tube 14 with a length of 11 mm in comparison with the reproducibility value attained with an arrangement without tube 14.

Reproducibility tests have been carried out using a tube 14 having a length of 33 mm and a diameter of 1.5 mm, and with a tube 14 of the same length but with a square cross-section of 1.5 mm × 1.5 mm, for several flash tubes of the same type and for flash tubes of different types. For these tests the sample cell 22 has been replaced by an optical filter the absorbance of which increases from 0.4 to 2 for a wavelength variation of 10 nm.

The following typical deviations of the absorbance variation have been obtained by the above tests:

| without tube 14 | with tube 14 |
|---|---|
| $\sigma = 2.10^{-3}$ to $4.10^{-3}$ | $\sigma = 3.10^{-4}$ to $5.10^{-4}$ |

These results show the considerable improvement of the reproducibility $\sigma$ obtained by use of tube 14 to stabilize the spatial distribution of the light intensity at the inlet-slot of the monochromator.

Figure 8B:
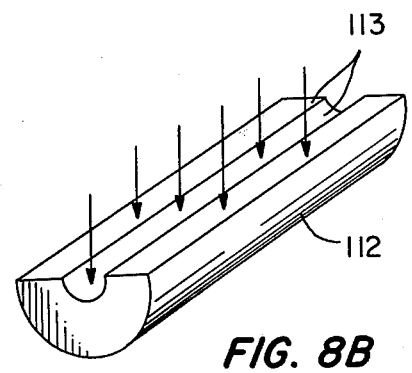
FIGS. 8a and 8b show a preferred construction of tube 14 in FIG. 1.
Figure 8A:
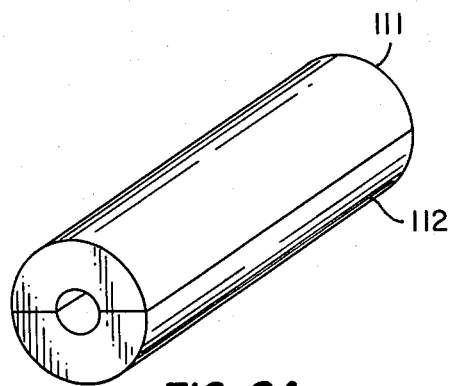

A preferred construction of tube 14 consists in the assembly of two half-cylinders 111, 112 (FIG. 8), the internal walls of which are coated by evaporation with a reflecting coating, e.g. an aluminium coating with a protective layer of magnesium fluoride. The half-cylinders 111,112 may be made of glass, a metal or moulded plastic. Tube 14 can in this way be manufactured to a reasonable price and can attain an acceptable life duration.

To avoid deterioration of tube 14 the focussing lens 13 (FIG. 1) is preferably placed so as to close the optical inlet of tube 14. In a similar way a quartz plate or a lens of short focal length, which forms the image of a section of tube 14 where the beam is stable at the inlet slit of the monochromator, is placed so as to close the outlet of tube 14.

Tube 14 constitutes a particularly advantageous means to improve the reproducibility of the measurements performed with the spectrophotometer, in particular for high values of absorbance and outside of the peak value of absorbance of the measured sample. Furthermore, the requirements on the stability of the spatial position of the arc in the flash tube are less rigorous.

Figure 7:
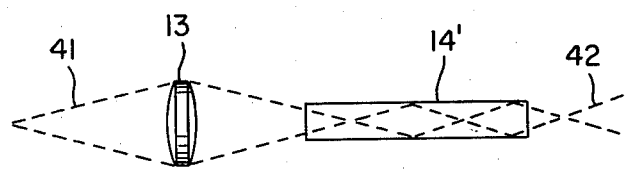
FIG. 7 is a diagrammatic view of part of a second device for obtaining a stable beam in the optical system in FIG. 1.

Tube 14 of the beam stabilizing device can also be constructed with different means, e.g. using a quartz cylinder 14' where the light rays are mixed by total reflection on the walls of the cylinder (see FIG. 7); alternatively a bundle of entwined optical fibres can also be used as stabilizing device.

The operation of the stabilizing device in the spectrophotometer according to the invention can easily be understood if one considers the difficulties of using an assembly which does not comprise such a device, i.e. an assembly (see FIG. 9) in which the image of the flash provided by the lamp is directly formed on the inlet slit of the grating monochromator.

Figure 10A:
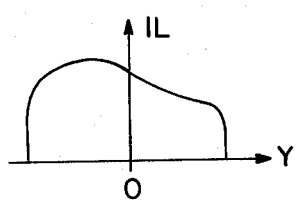
Figure 11A:
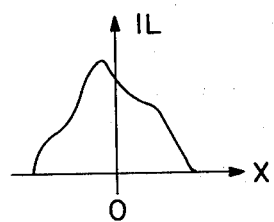
Figure 10B:
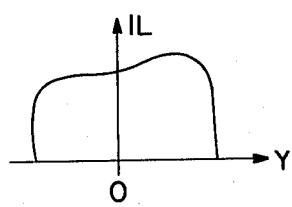
Figure 11B:
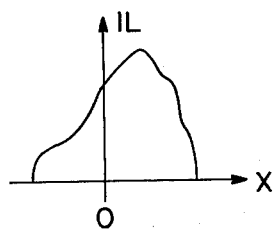

FIG. 9 shows a schematic representation of a such assembly. The image of each arc in the flash tube 11 is formed by lens 13 at the inlet slot of the monochromator. This image presents a certain distribution of light intensity IL, which distribution varies from one flash to the next in function of the position of the arc (see FIGS. 10a, 10b, 11a, 11b). FIGS. 10a, 10b show the variation of this distribution from one flash (FIG. 10a) to the next (FIG. 10b) in the diffraction plane ZOY. FIGS. 11a, 11b show the variation of the distribution of light intensity from one flash (FIG. 11a) to the next (FIG. 11b) in a plane ZOX perpendicular to the diffraction plane. If we consider variations in the distribution in the diffraction plane ZOY (the plane extending through the inlet slit, the outlet slit and the grating), the mean angle of rays coming from the slit and falling on the grid fluctuates with variations in the distribution of light energy on the slit. Since the wavelength of the light beam falling on the outlet slit depends on the angle of incidence of the rays, there is a variation in the selected mean wavelength. This results in poor reproducibility when the absorbance of the sample or the sensitivity of the detectors varies with the wavelength. Furthermore, in the plane perpendicular to the diffraction plane, variations in the position of the arc from one flash to the next also result in a variation in the mean position of the angle of the light beam, which changes the angle of incidence at the separating plate 17. Fresnel's laws of oblique reflection show that the coefficient of reflection depends on the angle of incidence and the polarization of light. A variation in the angle of incidence results in a variation in the coefficient of reflection, thus affecting the reproducibility of the measurements. To illustrate these variations, we shall assume that the mean position of the distribution of light is moved 0.1 mm on the inlet slot of the monochromator, corresponding to an angular variation of $5.9 \times 10^{-2}$ degrees for a mean angle of incidence of 45 degrees in a monochromator having a focal length of 100 mm. The angular variation results in a variation of the order of 0.2% in the ratio of light reflected by the plate to the transmitted light.

In addition, transmission in all media intercepted by the light beams (i.e. the measuring beam or the reference beam) may be subject to spatial irregularities, e.g. traces of powder or other impurities; in such cases, reproducibility is also affected by variations in the spatial distribution of the beam intensity from one flash to the next. Variations in spatial sensitivity of the detectors have a similar effect.

The aforementioned stabilizing device helps to reduce the negative effect of arc movements from one flash to the next on the reproducibility of measurements made with the spectrophotometer.

The monochromator used comprises a concave holographic grating 16. The grating 16 used in the present example is an holographic concave grating manufactured by Jobin-Yvon and having the following characteristics:

support dimensions: 32×32 mm
useful dimensions: 30×30 mm
number of lines: 1800 lines/mm
curvature radius: 99.96 mm
angle between arms: 42°
distance between inlet slit and grating: 95.8 mm
distance between grating and outlet slit: 98.7 mm The astigmatism of this grating is especially corrected for the wavelengths of 290 and 600 nm, but the astigmatism remains low outside these wavelengths. Masks such as 15 (see FIGS. 1 and 6) are disposed inside the monochromator so as to reduce interfering light due to reflection and diffusion on the monochromator walls. The inclination of the masks is chosen so that light not absorbed by the monochromator walls is reflected in directions such that it cannot reach the outlet slit. This assembly differs from conventional assemblies where the monochromator walls are perpendicular to the diffraction plane, so that non-absorbed light is reflected in directions where it can return to the grating and enter through the inlet slit. This applies particularly to the zero diffraction order in compact assemblies. Without the aforementioned masks, the interfering light due to zero diffraction order will be as great as the interfering light of the grating itself in the assembly herein described.

The separating plate 17 shown in FIG. 1 is a thin (e.g. approx. 0.2 mm) quartz plate. It divides the monochromator beam into a first beam, which travels through plate 17 and the sample 22 under analysis, and a second beam, which is reflected by the plate to a photodiode 18 which delivers a reference signal corresponding to the intensity of the second beam. This physical division of the monochromator beam is for compensating fluctuations in the energy limited by the flash. These fluctuations do not influence the spectrophotometer measurements, since they are calculated from the energy ratio between the beam emerging from the sample and the beam reaching photodiode 18.

As previously mentioned in the description of the operation of the device for stabilizing the beam sent to the inlet slot of the monochromator, variations in the position of the arc from one flash to the next result in a variation in the angle of incidence onto the separation plate 17 and a consequent variation in the coefficient of reflection thereof. The variation in the coefficient of reflection in turn affects the reproducibility of the measurements. In order to reduce the variations in the reflection coefficient of plate 17, it is advantageous to place the plate at right angles to the diffraction plane and at a small angle of incidence, since variations in the coefficient of reflection of the plate are very small at small angles of incidence. In order to place the separating plate at a small angle of incidence, e.g. between 10° and 25°, in particular about 14°, without complicating the optical assembly, the plate is placed inside the monochromator in the path of the convergent light beam travelling from the holographic grid 16 to the monochromator outlet slit 94 (in FIG. 6). This gives a convergent reference beam which reaches a slit corresponding to the outlet slit and then directly reaches the reference photodiode 18.

The optical system comprising lenses 19 and 21 forms an image of the monochromator grating on the sample inlet aperture and an image of the monochromator outlet slit on the sample outlet aperture. This configuration ensures optimum use of the light flux.

The order filters 24 disposed after the samples are coloured glass band-pass filters for eliminating light due to the fluorescence of some samples, light resulting from higher order of diffraction, and some of the interfering light.

Finally, the light flux through the sample is focused on photodiode 25, which delivers a signal corresponding to the intensity of the beam incident thereon.

The light current delivered by each photodiode is integrated for each light pulse, and the resulting signals are processed by a microprocessor after analog-digital conversion.

The embodiment described until here is particularly suitable for rotary analyzers; it uses a simple optical structure with few components. Owing to the very short flash (2.3 microseconds), there are no edge effects (i.e. light travelling along the cell walls) when the sample moves.

Figure 5:
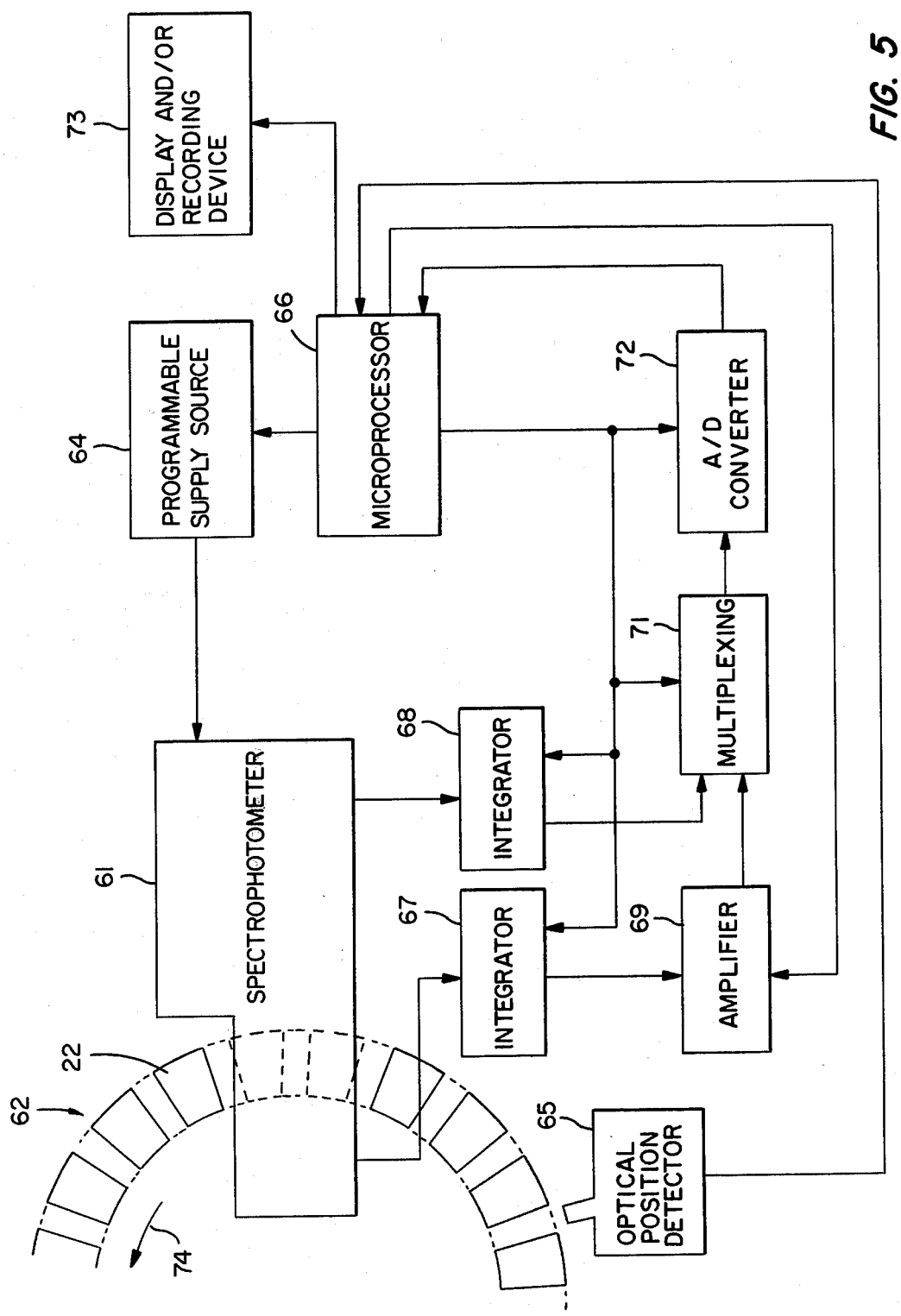
FIG. 5 is a block diagram showing the use of a spectrophotometer according to the invention in a rotary analyzer.

The block diagram in FIG. 5 illustrates the use of spectrophotometer 61 according to the invention (see FIG. 1) in a rotary analyzer comprising a rotor 62 containing the samples 22 shown in FIG. 1. An arrow 72 indicates the rotation of rotor 62 during the spectrophotometer measurements. A programmable supply source 64 energizes the flashlight 11 of spectrophotometer 61. The assembly is controlled and the results are calculated by a microprocessor 66. The action to be taken is initiated by microprocessor 66 when the selected sample is exactly in the axis of the light beam. This position is detected by an optical position detector 65 which detects marks on the rotor. An integrator 67 integrates the signal corresponding to the light beam received by photodiode 25 in FIG. 1, i.e. to the beam transmitted through sample 22. An integrator 68 integrates the signal corresponding to the light beam received by photodiode 18 in FIG. 1, i.e. the reference beam. An amplifier 69 having an automatically adjustable gain amplifies the output signal of integrator 67. Amplifier 69 is connected to microprocessor 66. A mutliplexing circuit 71 alternatively conveys the output of integrator 68 (reference signal) and amplifier 69 (the measuring signal) to an analog/digital converter 72 which converts the input analog signals and outputs them in digital form to microprocessor 66. Amplifier 69 automatically adapts the gain of the measured signal channel in dependence on the signal attenuation, so as to use that range of converter 72 which has the best resolution. The level of the incident or transmitted signal is also adjusted for optimum use of the converter, in dependence on the wavelength, by varying the voltage of the circuit 64 supplying the flash tube; this adjustment is also controlled by the microprocessor. Finally, the microprocessor makes all the required calculations, e.g. for determining the transmission, absorbance, the mean value of a number of measurements, and the concentration, and supplies signals corresponding to the measured results to a display and/or recording device 73. Double-beam spectrophotometers are used for compensating fluctuations in the intensity of the light source and undesirable drifts in the photometric characteristics of the sample, e.g. progressive variations in the absorbance of a reagent during certain clinical chemical analyses. To this end, the measurements are made with respect to a reference sample having the same drift as the sample being measured. Not many double-beam spectrophotometers comprise two physically distinct beams simultaneously supplying a reference signal and a measuring signal, since such devices are relatively expensive owing to the complexity of the optical system and the double light-detection system. It is more usual to have devices where the reference sample and the sample under test are measured in succession, using a mechanical means either for switching the light beam from one sample to another or for switching samples in front of a single beam. This method generally uses a single detection system and cannot compensate fluctuations in the intensity of the source between two successive measurements.

The use of a flash tube necessitates a system comprising two photodetector, but also permits the use of cheap silicon photodiodes, which have adequate photometric performance at high light intensity level with regard to the signal/noise ratio. In the case of rotary analyzers, the spectrophotometer according to the invention compensates undesirable photometric drifts by switching the reference sample and the sample under test. Switching results from the fact that when the rotor rotates, the spectropotometer produces signals representing absorption through (a) the samples under test and (b) at least one reference sample inserted between the samples under test disposed on the rotor.

Figure 4:
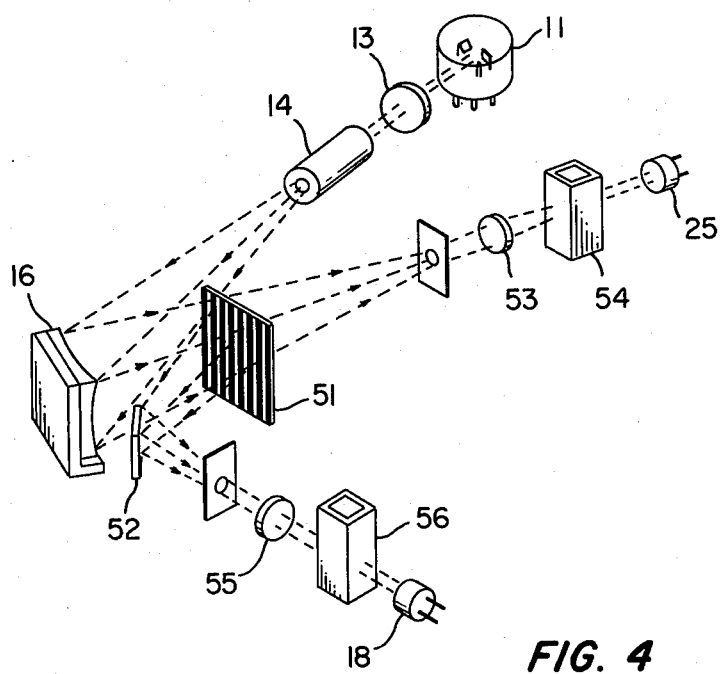
FIG. 4 is a diagram of a variant of the optical system in FIG. 1.

The spectrophotometer according to the invention described hereinbefore is particularly suited for rotary analyzers; it can be modified as diagrammatically shown in FIG. 4 to obtain a double-beam spectrophotometer which is of more general use and has advantages over known devices.

The variant of FIG. 4 shows a double-beam spectrophotometer without mechanical moving parts. The filtered beam is statically divided into two measuring beams. A sample can be placed in each beam. In this case, it is desired to obtain beams having substantially the same intensity. To this end, a Ronchi grating having a pitch of the order of 0.3 to 1 mm is placed on a quartz plate 51. This grating is chracterised by regularly alternating reflecting and transparent bands. As before, the beam travels through an outlet slit in the plate and then, via a lens 53, forms a light beam travelling through the reference sample 54 (the associated bandpass filter is not shown in FIG. 4) and falls on photodiode 25. The beam reflected by the plate is deflected at a return mirror 52 to an outlet slit and then, via a lens 55, continues its journey towards photodiode 18. Samples 56 for testing can be placed in the path of the reflected beam.

The device according to the invention is a double-beam spectrophotometer for general use, without moving mechanical parts, and has advantages resulting from the use of a flash tube and of a beam stabilizing device. By definition, however, this spectrophotometer can also be used for measuring transmission or absorbance of a wide variety of samples in a given spectral range, e.g. for conventional measurements of solutions used for clinical chemical analyses, in a static cell.

The optical measurements can relate to absorbance at a number of predetermined wavelengths or the recording of the transmission properties of the sample over a continuous spectral range. In the latter case, the value of the ratio of the signals obtained in the absence of a sample is previously stored in a microprocessor memory, so that the base level can be accurately subtracted, thus increasing the accuracy of measurement. In that case, the motion of the wavelength-selecting grating is controlled by a motor.

Figure 6:
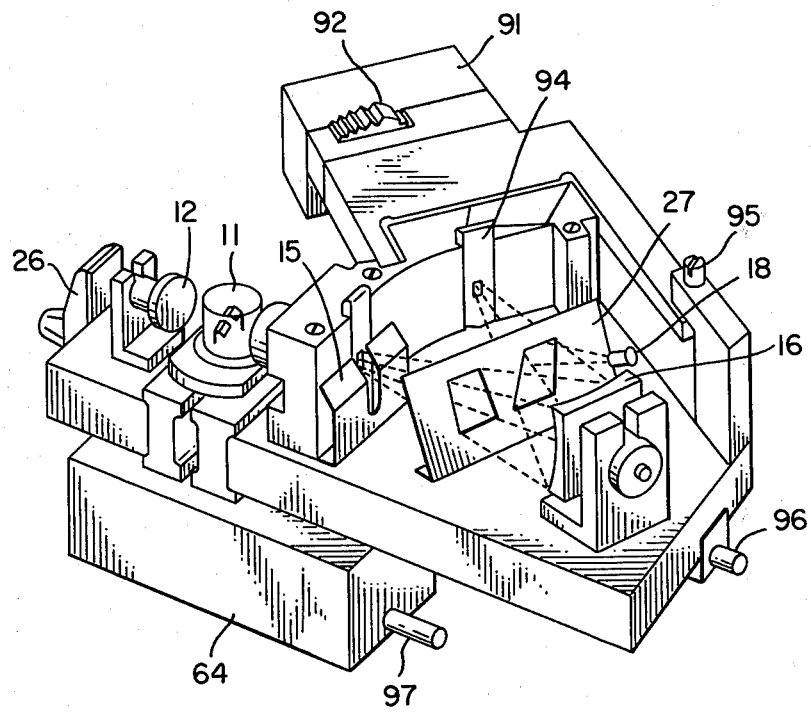
FIG. 6 is a perspective view showing the compact structure and small bulk of a spectrophotometer according to the invention.

One of the important advantages mentioned in the introduction to this description is that, as shown in FIG. 6, the spectrophotometer according to the invention is very compact with little bulk. In addition to the components previously defined with reference to FIG. 1, FIG. 6 shows a casing 91 containing a signal preamplifier corresponding to the intensity of the light flux transmitted through the sample, a selector 92 of order filters 24 (see FIG. 1), a plate containing the monochromator inlet slit, a plate 94 containing the outlet slit thereof, an adjusting screw 95 for adjusting the position of casing 91, a shaft 96 for selecting wavelengths via a motor, and a connection 97 to the supply network, if the supply source 64 is powered by the mains.

What is claimed is:

1. A spectrophotometer comprising:
   (a) a flash tube,
   (b) a stabilizing optical device for deriving from each flash from the flash tube a light beam having at the outlet of said device a spatial distribution which is substantially the same for every flash,
   (c) a grating monochromator for dispersing the light delivered by the stabilizing device and for delivering a beam of filtered light,
   (d) an optical element for driving the filtered beam to produce two beams, the first of which travels through a sample for analysis and the second of which reaches a detector which delivers a reference signal corresponding to the intensity of the second beam, and
   (e) a second detector placed to receive the beam emerging from the sample.

2. A spectrophotometer according to claim 1, wherein the flash tube comprises a starting electrode which is much nearer the cathode than the anode, in order to stabilize the position of the art.

3. A spectrophotometer according to claim 1, characterised in that the stabilizing device comprises a tube having reflecting internal walls for producing multiple reflections of the light beam from each flash.

4. A spectrophotometer according to claim 1, wherein the monochromator comprises a holographic concave grating.

5. A spectrophotometer according to claim 1, wherein the optical element for dividing the filtered beam is a thin quartz plate disposed so that the angle of incidence of the filtered beam is comprised between 10° and 25°.

6. A spectrophotometer according to claim 1, wherein optical element for dividing the filtered beam is a thin quartz plate comprising transparent and reflecting strips in alternation.

7. A spectrophotometer according to claim 1, wherein the stabilizing device comprises a quartz cylinder for producing multiple reflections of the light beam from each flash.

8. A spectrophotometer according to claim 1, wherein a reference or a measuring sample can be placed in each of the two filtered beams coming from the dividing element.

9. In an analyzer for performing clinical-chemical analysis, a spectrophotometer comprising:
   (a) a flash tube,
   (b) a stabilizing optical device for deriving from each flash from the flash tube a light beam having at the outlet of said device a spatial distribution which is substantially the same for every flash,
   (c) a grating monochromator for dispersing the light delivered by the stabilizing device and for delivering a beam of filtered light,
   (d) optical element means for dividing the filtered beam to produce two beams, the first of which travels through a sample for analysis and the second of which reaches a detector which delivers a reference signal corresponding to the intensity of the second beam, and
   (e) a second detector positioned to receive the beam emerging from the sample.

* * * * *